United States Patent [19]

Montalvo et al.

[11] Patent Number: 5,489,265
[45] Date of Patent: Feb. 6, 1996

[54] RESTRICTOR FITTING FOR AN INFUSION PUMP

[75] Inventors: Susan M. Montalvo; Rudolph A. Montalvo, both of Woodland Hills, Calif.

[73] Assignee: IVAC Corporation, San Diego, Calif.

[21] Appl. No.: 343,843

[22] Filed: Nov. 23, 1994

Related U.S. Application Data

[63] Continuation of Ser. No. 260,601, Jun. 15, 1994.

[51] Int. Cl.⁶ .................................................. A61M 5/00
[52] U.S. Cl. .................................................. 604/67
[58] Field of Search ........................ 604/4, 65, 67, 604/122–127; 128/DIG. 12, DIG. 13; 73/19.01, 19.03, 19.1; 138/41.44

[56] References Cited

U.S. PATENT DOCUMENTS

| | | | |
|---|---|---|---|
| 1,144,040 | 6/1915 | Keller | 138/41 |
| 1,298,471 | 3/1919 | Dodge | 138/44 |
| 1,559,156 | 10/1925 | Bullock | 138/44 |
| 1,681,725 | 8/1928 | Donnelly | 138/44 |
| 2,486,133 | 10/1949 | Egger | 138/41 |
| 2,576,610 | 11/1951 | Kunzog | 138/41 |
| 3,724,502 | 4/1973 | Hayner et al. | 138/41 |
| 3,792,609 | 2/1974 | Blair et al. | 138/41 |
| 3,898,637 | 8/1975 | Wolstenholme | 604/123 |
| 4,037,596 | 7/1977 | LeFevre et al. | 138/44 |
| 4,105,721 | 8/1978 | Schliebe | 138/44 |
| 4,155,362 | 5/1979 | Jess | 128/DIG. 12 |
| 4,181,610 | 1/1980 | Shintani et al. | 604/31 |
| 4,244,365 | 1/1981 | McGill et al. | 604/123 |
| 4,344,429 | 8/1982 | Gupton et al. | 604/67 |
| 4,535,818 | 8/1985 | Duncan et al. | 604/122 |
| 4,834,108 | 5/1989 | Vaillancourt | 604/126 |
| 5,026,348 | 6/1991 | Venegas | 604/122 |
| 5,045,096 | 9/1991 | Quang et al. | 604/126 |
| 5,085,058 | 2/1992 | Aaron et al. | 138/44 |

FOREIGN PATENT DOCUMENTS

| | | | |
|---|---|---|---|
| 23055 | 10/1955 | Germany | 138/44 |
| 8901796 | 3/1989 | WIPO | 604/122 |

OTHER PUBLICATIONS

Gerhart et al, *Fundamentals of Fluid Mechanics*, Addison–Wesley Pub. Co., pp. 484–491, 1985.

Avallone et al, *Marks' Standard Handbook for Mechanical Engineers*, 9th Ed., McGraw–Hill Book Co., pp. 3.54–3.67, 1989.

Primary Examiner—C. Fred Rosenbaum
Assistant Examiner—Manuel Mendez
Attorney, Agent, or Firm—Fulwider Patton Lee & Utecht

[57] ABSTRACT

A restrictor fitting is provided at the discharge side of an infusion pump to substantially reduce or eliminate the presence of undissolved gas such as air within the detection field of an air-in-line sensor. The restrictor fitting defines a flow orifice of reduced cross-sectional size disposed along an infusion line in close proximity with a pump discharge port, and at a position slightly downstream from the air-in-line sensor. The restrictor fitting maintains an infusion liquid under substantially constant pressure conditions, with minimal pressure drop across the sensor detection field, and thereby minimizes the occurrence of undissolved gas attributable to outgassing at that location. In addition, the flow orifice acts as a bubble trap to prevent backflow of gas bubbles to the sensor detection field.

11 Claims, 3 Drawing Sheets

RESTRICTOR FITTING FOR AN INFUSION PUMP

This application is continuation, of application Ser. No. 08/260,601*, filed Jun. 15, 1994.
*Ser. No. 08/260,601 Filed Jun. 15, 1994 is a continuation of Ser. No. 07/852616 Filed Mar. 13, 1992.

IDENTIFICATION OF RELATED PATENT APPLICATION

This application is related to a concurrently filed copending patent application. This patent application is U.S. patent application Ser. No. 07/852,626, entitled "Infusion System With Air-In-Line Clear Function," now abandoned. This application is hereby incorporated herein by reference.

1. Background of the Invention
2. Field of the Invention

The present invention relates generally to medical fluid infusion systems for delivering one or more selected medical fluids to a patient, and more particularly to a relatively simple yet effective flow restrictor device for minimizing the occurrence of undissolved gas such as air within the detection field of an air-in-line sensor, and the occurrence of air-in-line alarms associated therewith.

Medical fluid infusion systems are generally known in the art for use in delivering one or more selected medical liquids through appropriate tubing and/or a catheter or the like to a patient. Such infusion systems often utilize a relatively compact electronically controlled pump adapted for mounting onto a conventional portable medical equipment pole and including one or more appropriate pump elements for closely regulating fluid delivery to the patient. One example of an infusion pump of this general type is marketed by MiniMed Technologies of Sylmar, Calif. under the name MiniMed III.

Modern infusion pumps used in patient fluid infusion systems are commonly equipped with an air-in-line sensor for monitoring fluid delivery through a length of tubing and to activate an alarm and/or disable the pump upon detection of air. In this regard, ultrasonic detectors are known in the art and have the capability to determine the volume of air in an infusion line and to activate the alarm or halt pump operation when the detected air volume exceeds a predetermined and potentially harmful threshold. Such air detectors may operate in conjunction with the pump to decrement an accumulated fluid infusion record in accordance with the volume of air detected within the infusion line.

Relatively small air or gas bubbles occur most commonly along the infusion line at a position closely adjacent to a discharge port of the associated pump element. Accordingly, the air-in-line sensor is typically mounted with its detection field encompassing the infusion line directly at the discharge side of the pump. In most instances, however, the volume of undissolved gas present within the infusion line, and within the detection field of the air-in-line sensor, is sufficiently small such that no significant patient hazard results and there is no need to interrupt pump operation. Such small volumes of undissolved gas are apparently the result of complex fluid flow and pressure factors which have a tendency to enhance outgassing at the discharge side of the infusion pump. Although many air-in-line sensors can be adjusted to permit flow-through passage of small gas quantities without activating an alarm or stopping pump operation, such small bubbles sometimes become stuck or trapped within the sensor detection field and result in false alarms requiring the attention of medical personnel.

The present invention overcomes the problems and disadvantages encountered in the prior art by providing a flow restrictor fitting in conjunction with an infusion pump with an air-in-line sensor, wherein the flow restrictor fitting effectively minimizes or eliminates the occurrence of small gas bubbles attributable to outgassing effects within the sensor detection field. In addition, the restrictor fitting effectively prevents undissolved gas from backflowing along the infusion line to the sensor detection field.

SUMMARY OF THE INVENTION

In accordance with the invention, a restrictor fitting is provided along an infusion line at the discharge side of an infusion pump, at a position slightly downstream of an air-in-line sensor. The restrictor fitting defines a flow orifice of reduced cross-sectional size for substantially minimizing or eliminating the occurrence of small gas bubbles within the detection field of the sensor. The restrictor fitting functions further as a bubble trap to substantially preclude backflow of gas bubbles along the infusion line to the sensor detection field.

The restrictor fitting is adapted for in-line connection along the length of an infusion line through which a medical liquid is administered under controlled flow conditions from an infusion pump to a patient. The restrictor fitting is mounted along the infusion line at a position in close proximity with the discharge side of the infusion pump, and in a manner accommodating the air-in-line sensor with its associated detection field at a position between the restrictor fitting and the pump. The restrictor fitting provides the flow orifice of reduced cross-sectional size which effectively maintains a substantially constant fluid pressure throughout the sensor detection field, for correspondingly minimizing the nucleation of small air bubbles as a result of outgassing from the liquid. In addition, the flow orifice prevents undesired backflow of undissolved gas along the infusion line in an upstream direction to the sensor detection field.

In a preferred form, the flow orifice is shaped to facilitate flow-through passage of gas bubbles in the downstream direction, yet substantially prevent backflow of such bubbles in the upstream direction. In particular, the preferred orifice shape includes a conically tapered inlet segment which reduces in cross-sectional size in a downstream-flow direction to merge with a short outlet segment of cylindrical shape. The cylindrical outlet segment may extend in a downstream direction to define a short cylindrical nipple spaced concentrically within a cylindrical body of the restrictor fitting. In an alternative preferred form, the flow orifice can be defined by a mesh screen element having a plurality of small flow openings formed therein, wherein the screen element effectively reduces the cross-sectional size of the fluid flow path to maintain the pressure across the sensor detection field, with said small flow ports cooperatively resisting gas bubble backflow. The mesh screen element may be combined with a fitting body having a conically tapered inlet segment leading to a cylindrical outlet segment of reduced cross-sectional size having the screen element mounted therein.

Other features and advantages of the present invention will become more apparent from the following detailed description, taken in conjunction with the accompanying drawings which illustrate, by way of example, the principles of the invention.

DESCRIPTION OF THE DRAWINGS

These and other advantages of the present invention are best understood with reference to the drawings, in which.

DETAILED DESCRIPTION OF THE PREFERRED EMBODIMENTS

Figure 1:
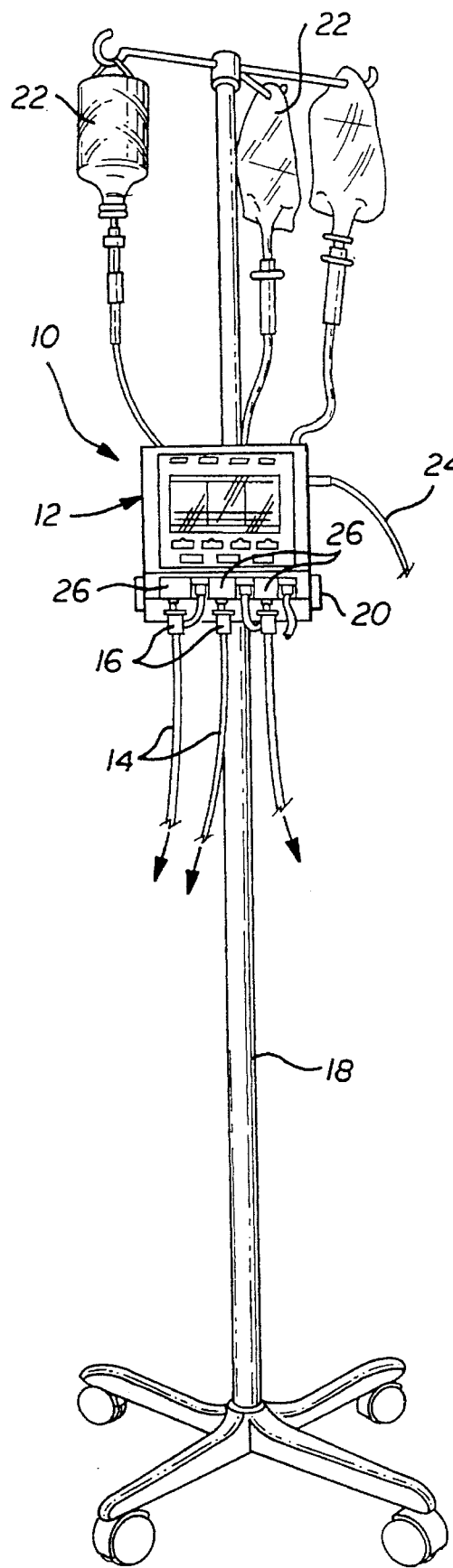
FIG. 1 is a fragmented front perspective view illustrating an infusion pump incorporating a restrictor fitting embodying the novel features of the invention.

As shown in the exemplary drawings, a medical fluid infusion system referred to generally in FIG. 1 by the reference numeral 10 is provided for delivering one or more medical liquids to a patient (not shown) under controlled, closely regulated flow conditions. The infusion system 10 includes an infusion pump 12 for delivering the medical liquid or liquids through respective infusion tubing or lines 14 to the patient. A flow restrictor fitting 16 in accordance with the invention is provided at the discharge side of the pump 12 for substantially reducing or eliminating the presence of undissolved gas in the form of bubbles within the detection field of an air-in-line sensor.

Figure 2:
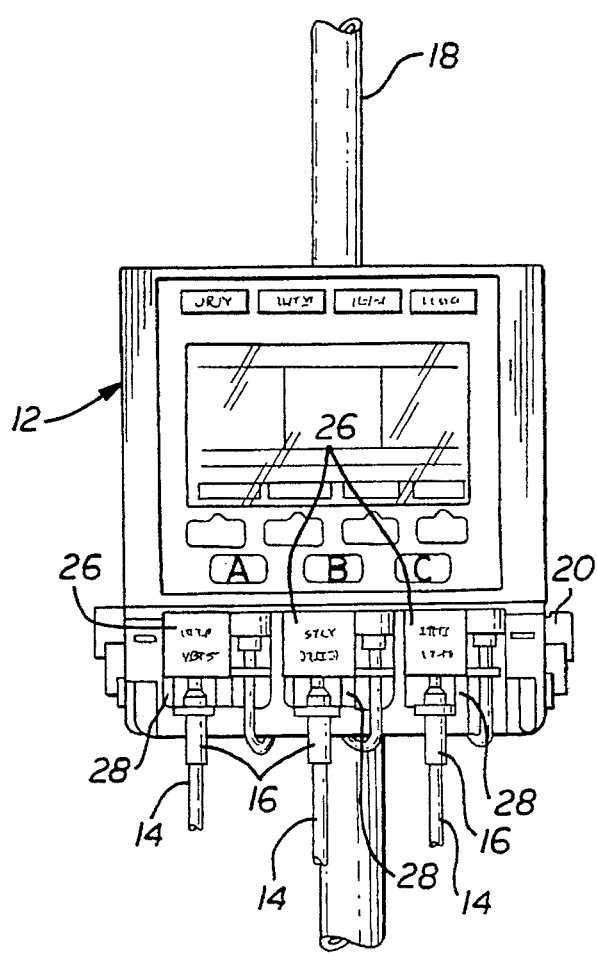
FIG. 2 is an enlarged front elevational view of the infusion pump depicted in FIG. 1.

FIGS. 1 and 2 illustrate the infusion pump 12 in the form of a compact medical instrument adapted for mounting onto a conventional medical equipment pole 18 by means of an appropriate adjustable clamp bracket 20 or the like. The illustrative infusion pump 12 includes multiple parallel fluid delivery channels for independent programming control to regulate administration of one or more medical liquids from appropriate reservoirs 22 via the infusion lines 14 to a patient. Electronic control components and associated mechanical pumping devices are integrated into the pump 12 and normally operated upon connection of the instrument to an appropriate power supply, as by means of a power cord 24. In a preferred form, the infusion pump comprises a compact and multiple channel pump adapted for operation with disposable pump elements or cassettes 26 of the type utilized in the MiniMed III fluid infusion pump marketed by MiniMed Technologies of Sylmar, Calif. A more detailed disclosure of the construction and operation of the MiniMed III pump is found in U.S. Pat. No. 5,000,663, which is incorporated by reference herein.

In a fluid infusion pump 12 of this general type, each pump element 26 (FIGS. 2 and 3) is normally associated with an air-in-line sensor 28 disposed substantially at the discharge side or discharge outlet port 30 of the associated pump element for monitoring the medical liquid for the presence of undissolved air or gas. In this regard, such air-in-line monitoring is necessary or desirable to prevent infusion of potentially harmful quantities of air or gas into the patient. The air-in-line sensor 28 is adapted to respond to a substantial detected volume of undissolved gas in the liquid stream at the discharge side of the pump element to activate a visual and/or audio pump alarm, and/or to halt operation of the corresponding pump channel, pending correction of the air-in-line condition by attending medical personnel. For example, air-in-line sensors may be used to place the pump in an alarm mode or in a stop mode when preset threshold levels of undissolved gas are detected. Although different types of such sensors are known, an ultrasonic type sensor is preferred.

During normal pump operation, relatively minor quantities of air or gas are often detected within the liquid flow stream, wherein such minor gas quantities are predominantly the result of outgassing from the liquid or diffusion of air through system components. Such minor gas quantities are detected most commonly at the discharge side of the pump, as an apparent result of pressure fluctuations and/or pumping agitation. To prevent the detection of such minor air quantities within the detection field of the air-in-line sensor 28, and thereby avoid the occasional and annoying false alarms associated therewith, the flow restrictor fitting 16 of the present invention is provided to substantially prevent the occurrence of such minor gas quantities within the sensor detection field.

Figure 3:
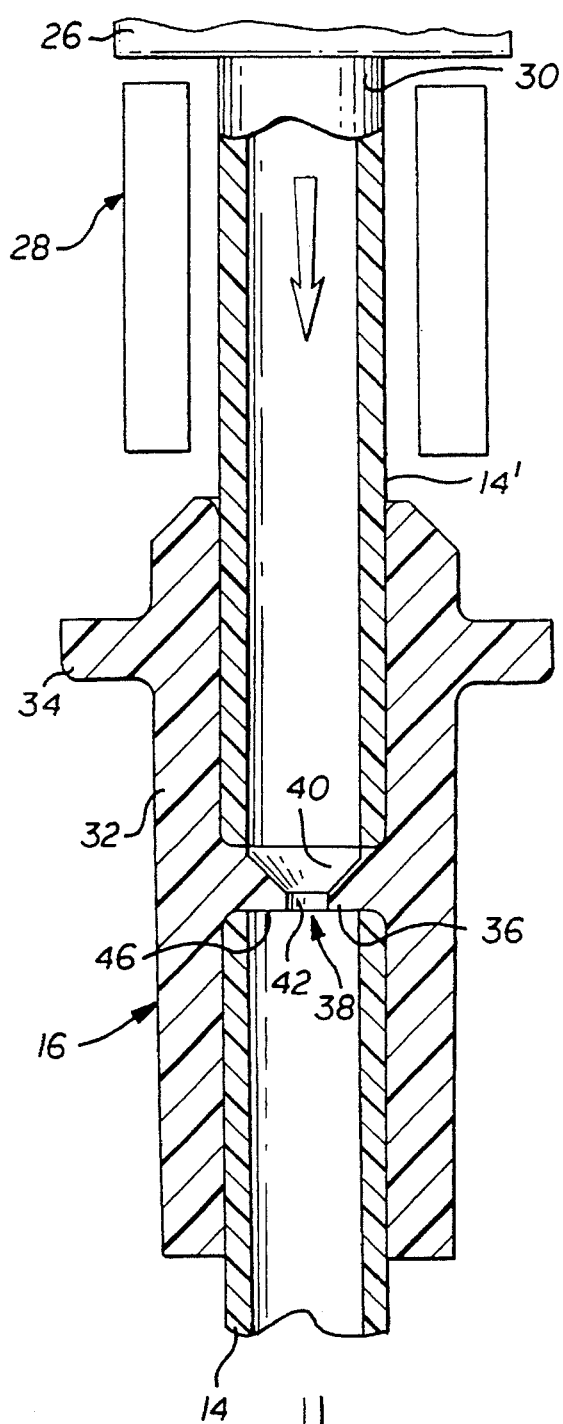
FIG. 3 is a further enlarged fragmented sectional view illustrating the restrictor fitting in one preferred form, in conjunction with an infusion pump and associated air-in-line sensor.
Figure 4:
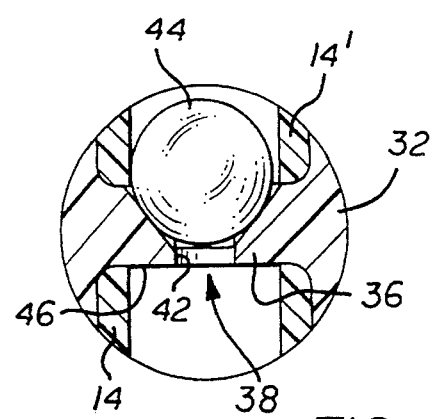
FIGS. 4 is the first of four enlarged fragmented sectional views depicting sequential movement of a gas bubble through the restrictor fitting of FIG. 3.
Figure 5:
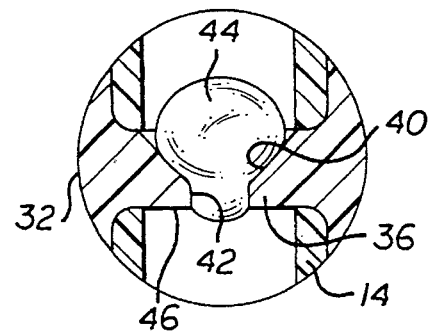
FIGS. 5 is the second of four enlarged fragmented sectional views depicting sequential movement of a gas bubble through the restrictor fitting of FIG. 3.
Figure 6:
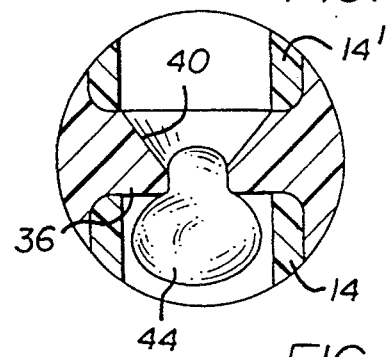
FIGS. 6 is the third of four enlarged fragmented sectional views depicting sequential movement of a gas bubble through the restrictor fitting of FIG. 3.
Figure 7:
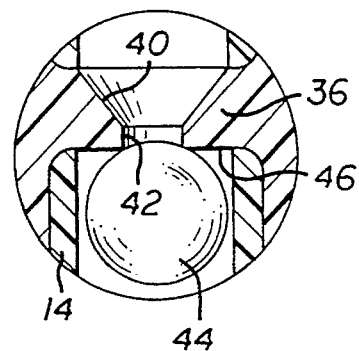
FIGS. 7 is the last of four enlarged fragmented sectional views depicting sequential movement of a gas bubble through the restrictor fitting of FIG. 3.

FIG. 3 illustrates the flow restrictor fitting 16 in one preferred form to include a hollow cylindrical body 32 having a radially enlarged external flange 34 near an inlet end thereof to facilitate manual handling and correct in-line installation along the length of the infusion line 14. A short discharge segment 14' of the infusion line is connected to the discharge side or discharge port 30 of the associated pump element 26 for receiving the medical liquid discharged from the pump. This discharge segment 14' has its downstream end seated within one end of the restrictor body 32 in substantial abutting relation with a radially inwardly projecting annular wall 36. The opposite end of the restrictor body 32 receives the end of the infusion line 14 in substantial abutting relation with an axially opposed face of the internal annular wall 36. Secure seated attachment of the infusion line 14, 14' within the flow restrictor fitting 16 is quickly and easily obtained as by solvent bonding or the like. Importantly, the lengths of the infusion line 14, 14' define a substantially constant cross-sectional diameter for flow of the medical liquid therethrough.

The annular internal wall 36 of the flow restrictor fitting 16 defines a flow orifice 38 of reduced cross-sectional size for passage of the medical liquid discharged from the infusion pump 12. This reduced-size orifice 38 functions, during normal operation of the infusion pump, to maintain a substantially constant fluid pressure zone extending from the fitting wall 36 in an upstream direction to the discharge side 30 of the pump 12. This zone of substantially constant fluid pressure extends over and encompasses the detection field of the air-in-line sensor 28 mounted between the discharge side 30 of the infusion pump and the enlarged outer flange 34 on the restrictor fitting 16. Accordingly, with this arrangement, substantial pressure drops associated normally with the pump discharge side are avoided throughout the sensor detection field, to correspondingly avoid nucleation of outgassing bubbles at that location. Instead, the pump liquid does not encounter a substantial pressure drop until passage through the flow orifice 38 at a location downstream from the sensor 28.

The preferred geometry for the flow orifice 38 comprises a conically converging tapered inlet segment 40 leading to an outlet segment 42 having a short substantially constant cross-section cylindrical shape. With this geometry, microbubbles if generated upstream from the flow orifice 38 are guided with a slight turbulent and swirling action through the conical inlet segment 40 for positive passage through the flow orifice 38 to a downstream location. In this regard, the leading edge of the conical inlet segment 40 is sized for substantial diametric match with the internal diameter of the line segment 14', thereby avoiding any internal flow surfaces extending substantially at a right angle to the direction of fluid flow. This geometry effectively eliminates surface sites on the infusion line 14' whereat small gas bubbles could otherwise become trapped and collect within the detection field of the air-in-line sensor 28.

FIGS. 4–7 further illustrate the preferred geometry for the flow orifice 38 to facilitate passage of gas bubbles to a downstream location. In particular, with respect to a relatively large gas bubble 44, the bubble smoothly enters the conical inlet segment 40 of the orifice 38 and is compressed by the liquid flow to squeeze through the orifice for relatively smooth passage to a downstream location. As soon as bubble 44 passes beyond the flow orifice 38, the bubble resumes a substantially spherical configuration which, if subjected to backflow conditions, is effectively blocked by the internal fitting wall 36 from passage in an upstream direction through the flow orifice 38. That is, the annular internal wall 36 has a downstream face 46 extending generally perpendicularly to the direction of fluid flow whereby the downstream face 46 functions to effectively block relatively large bubbles from backflow passage through the orifice. Similarly, this perpendicular downstream face 46 effectively blocks microbubbles which may tend to collect along the interior wall surfaces of the infusion line 14 from return passage through the orifice 38.

Figure 8:
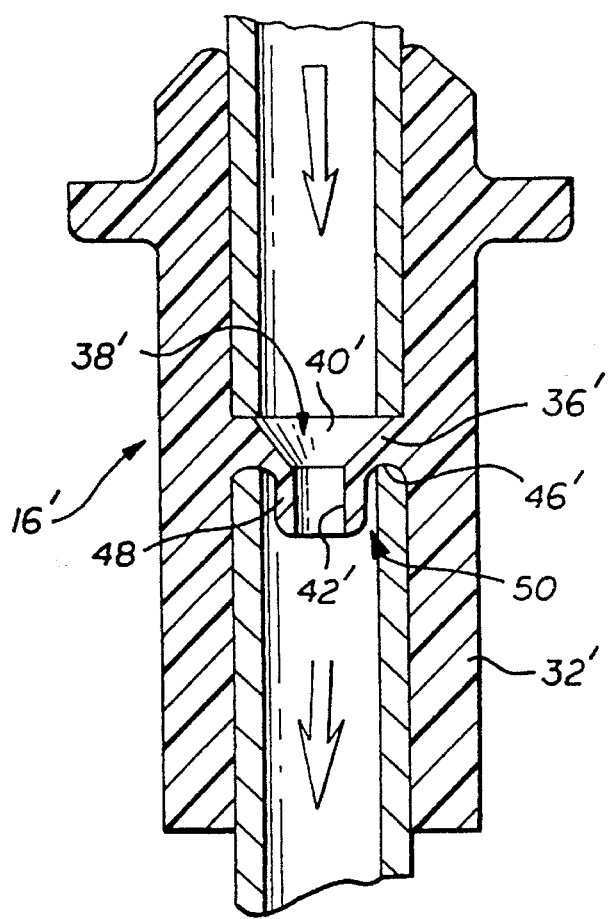
FIG. 8 is an enlarged sectional view depicting an alternative preferred form for a restrictor fitting embodying the invention.

FIG. 8 illustrates one alternative preferred form of the restrictor fitting, wherein components identical to those shown and described in FIGS. 3–7 are identified by common prime reference numerals. In this embodiment, the overall construction and operation of a modified flow restrictor 16' is the same as previously described, except that the cylindrical outlet segment 42' of the flow orifice 38' is formed within an axially extended cylindrical nipple 48 which projects in a downstream direction beyond the downstream face 46' of the internal fitting wall 36'. The nipple 48 thus cooperates with the fitting body 32' and the wall 36' to define an annular recessed trap 50 which opens in an axially downstream direction for collecting any small gas bubbles which may tend to migrate along the infusion line in an upstream direction, particularly as a result of gravity.

Figure 9:
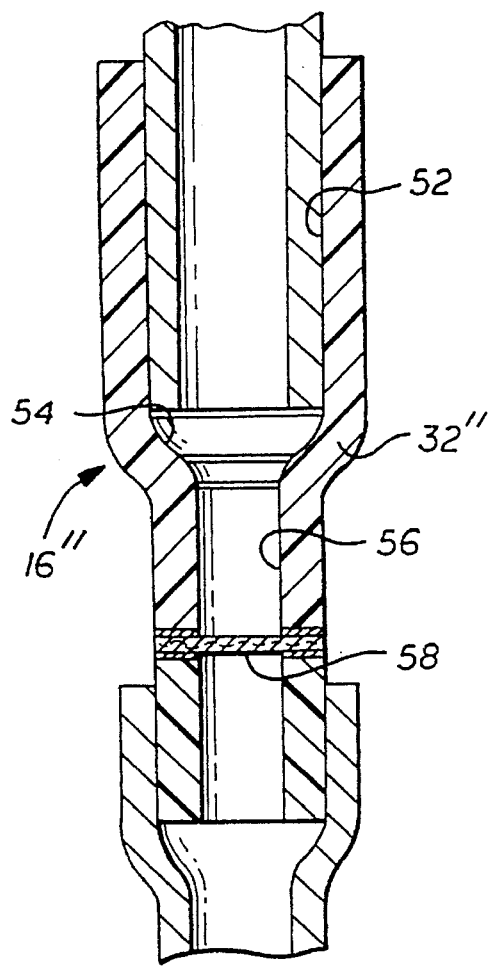
FIG. 9 is an enlarged fragmented sectional view depicting another alternative preferred from of the invention.

A further alternative preferred form of the invention is shown in FIG. 9 wherein a modified flow restrictor fitting 16" includes a shaped fitting body 32" having an upstream flow passage 52 of a cross-sectional dimension for insert mounting of the infusion line segment extending through the detection field of the air-in-line sensor, in the same manner as previously described. This upstream flow passage 52 merges through a conically tapered segment 54 with a downstream flow passage 56 of smaller cross-sectional area adapted for mounted reception into the end of the infusion line leading to the patient. Within the downstream segment 56, a mesh screen element 58 is mounted for flow-through passage of the liquid stream and any air entrained therewith. The screen element 58 defines a large plurality of small flow orifices each having a size sufficient for passage of the liquid material and any gas bubbles associated therewith in response to positive pressure pumping action of the infusion pump. Any bubbles, if too large to pass through a single screen pore, will be broken up under the pumping action for passage through the screen element to a downstream location. However, the structure of the screen element provides a sufficient flow restriction to maintain the fluid pressure substantially constant, without significant pressure drop, across the detection field of an air-in-line sensor. The small pores of the screen element additionally provide an effective bubble trap to resist bubble backflow to the sensor detection field. Although the specific size and number of the screen pores may vary, a screen element having pores within the range of about 10–15 microns to about 1000 microns is contemplated, with a preferred pore size on the order of about 200 microns.

The restrictor fitting of the present invention thus provides a relatively simple and easy to use yet effective device for minimizing or eliminating the occurrence of minor air volumes within the detection field of an air-in-line sensor, in a medical fluid infusion system. The restrictor fitting maintains fluid pressure across the sensor detection field to minimize the likelihood of out gassing within the detector field range. In addition, the flow restrictor fitting is shaped to accommodate passage of small or large gas bubbles, while providing an obstruction which substantially prevents gas backflow to the detection field of the air-in-line sensor.

A variety of further modifications and improvements to the invention shown and described herein will be apparent to those skilled in the art. Accordingly, no limitation on the invention is intended by way of the foregoing description of the accompanying drawings, except as set forth in the appended claims.

What is claimed is:

1. A medication infusion system for delivering a medical fluid to a patient, the system comprising:

an infusion line adapted to be connected to the patient for delivering the medical fluid to the patient;

a pump operating on the infusion line to pump the medical fluid through the infusion line to the patient, the pump having a pump discharge outlet for delivery of the medical fluid through said infusion line under controlled flow conditions;

an air-in-line sensor mounted to the pump at the discharge side and having a detection field adapted to receive a short length of said infusion line at the discharge side of said pump and including means for detecting gas bubbles within said short length of the infusion line and for responding thereto to activate an alarm; and a restrictor mounted in said infusion line and coaxial therewith at a position downstream of the sensor detection field and downstream of the discharge outlet of the pump, said restrictor having a surface defining an orifice formed through its length and permanently fixed in size and shape to provide a fluid flow path through the restrictor, the orifice having an upstream segment with an internal surface defining a frusto-conical shape with a smaller diameter at a downstream end of said upstream segment, the orifice further having a cylindrical segment having an inner surface defining a generally cylindrical shape disposed in line with and in contact with the downstream end of the upstream segment, the cylindrical segment having an external downstream side surface for blocking the passage of bubbles upstream through said orifice.

2. The medication infusion system as claimed in claim 1, wherein the orifice of the upstream segment of the restrictor has a diametric size at its upstream side substantially matching the diametric size of the fluid flow path defined by said infusion line through said sensor detection field.

3. The medication infusion system as claimed in claim 1, wherein the external downstream side surface of the cylindrical segment of the restrictor further defines a nipple having a length and an outer diameter, the nipple extending into the fluid line, the outer diameter of the nipple being less than the inner diameter of the fluid line so that an annular bubble trap is defined between the outer diameter of the nipple and the inner diameter of the fluid line along the length of the nipple.

4. A medication infusion system for delivering a medical fluid to a patient, the system comprising:

an infusion line adapted to be coupled to the patient for delivering the medical fluid to the patient;

a pump operating on the infusion line to pump the medical fluid through the infusion line to the patient, the pump having a pump discharge outlet for delivery of the medical fluid through said infusion line under controlled flow conditions;

an air-in-line sensor mounted to the pump at the discharge side and having a detection field adapted to receive a short length of said infusion line at the discharge side of said pump and including means for detecting gas bubbles within said short length of the infusion line and for responding thereto to activate an alarm; and a restrictor mounted in said infusion line and coaxially therewith at a position downstream of the sensor detection field and downstream of the pump discharge outlet, said restrictor having a generally tubular body with a radially inwardly extending mesh screen element being located in said generally tubular body, said mesh screen element having a large plurality of small pores formed therein, said plurality of small pores cooperating to form a flow orifice, said mesh screen element also acting to break up large bubbles into smaller bubbles for conveyance downstream in said infusion line and to resist backwards flow of bubbles through said restrictor.

5. An infusion system for delivering a selected medical liquid to a patient, said system comprising:

an infusion line adapted to be connected to the patient for delivering the medical liquid to the patient;

an infusion pump having a pump discharge outlet for delivery of the medical liquid through said infusion line under controlled flow conditions;

an air-in-line sensor having a detection field disposed in close proximity with said pump discharge outlet and having a short length of said infusion line disposed within said detection field, said sensor including means for detecting undissolved gas within said short length of the infusion line and for responding thereto to activate an alarm; and a restrictor mounted in said infusion line and coaxially therewith at a position downstream of the sensor detection field and downstream of the pump discharge outlet, said restrictor having an orifice formed through its length and permanently fixed in size and shape to provide a fluid flow path through the restrictor, the orifice having an upstream segment having an internal surface defining a frusto-conical shape with a smaller diameter end at a downstream end of said upstream segment, the orifice further having a downstream cylindrical segment having an inner surface defining a generally cylindrical shape disposed in line with and in contact with the downstream end of the upstream segment, the cylindrical segment having an external downstream side surface for blocking the passage of bubbles upstream through said orifice, wherein the orifice of the upstream segment of the restrictor has a diametric size at its upstream side substantially matching the diametric size of the fluid flow path defined by said infusion line through said sensor detection field, and the length of the upstream segment exceeds the length of the cylindrical segment.

6. The infusion system as defined in claim 5, wherein the external downstream side surface of the cylindrical segment of the restrictor further defines a nipple having a length and an outer diameter, the nipple extending into the fluid line, the outer diameter of the nipple being less than the inner diameter of the fluid line so that an annular bubble trap is defined between the outer diameter of the nipple and the inner diameter of the fluid line along the length of the nipple.

7. The infusion system of claim 1 wherein the length of the frusto-conical shaped segment exceeds the length of the cylindrical shaped segment.

8. The medication infusion system as claimed in claim 1, further comprising:

a positioning flange formed on the outer surface of the restrictor;

a tapered portion located at a top end of the restrictor with the taper being on the outside of the restrictor and having a smaller outer diameter as it approaches the top end of the restrictor for ensuring correct in-line installation of the restrictor and the infusion line adjacent the air-in-line sensor.

9. The infusion system as defined in claim 6, further comprising:

a positioning flange formed on the outer surface of the restrictor;

a tapered portion located at a top end of the restrictor with the taper being on the outside of the restrictor and having a smaller outer diameter as it approaches the top end of the restrictor for ensuring correct in-line installation of the restrictor and the infusion line adjacent the air-in-line sensor.

10. The infusion system of claim 1, wherein said external downstream side surface extends substantially at a right angle to the direction of flow through the restrictor.

11. The infusion system of claim 5, wherein said external downstream side surface extends substantially at a right angle to the direction of flow through the restrictor.

* * * * *

UNITED STATES PATENT AND TRADEMARK OFFICE
CERTIFICATE OF CORRECTION

PATENT NO. : 5,489,265
DATED : February 6, 1996
INVENTOR(S) : Susan M. Montalvo, Rudolph A. Montalvo It is certified that error appears in the above-indentified patent and that said Letters Patent is hereby corrected as shown below:

On the title page:

Item [63]: Related U.S. Application Data, change "Continuation of Ser. No. 260,601, Jun. 15, 1994" to read --Continuation of Ser. No. 260,601, Jun. 15, 1994, abandoned, which is a continuation of Ser. No. 852,616, Mar. 13, 1992, abandoned.--

Column 1, line 12, change "07/852,626" to read --07/852,622--.

Column 1, line 13, delete "now abandoned" and insert --now U.S. Patent No. 5,382,232--

Signed and Sealed this

Twenty-sixth Day of August, 1997

Attest:

BRUCE LEHMAN

*Attesting Officer*          Commissioner of Patents and Trademarks